United States Patent [19]

Shimizu et al.

[11] Patent Number: 5,221,766
[45] Date of Patent: Jun. 22, 1993

[54] METHOD FOR PRODUCING α-(P-ISOBUTYLPHENYL) PROPIONIC ACID

[75] Inventors: Isoo Shimizu; Yasuo Matsumura, both of Kanagawa, Japan

[73] Assignee: Nippon Petrochemicals Company, Limited, Tokyo, Japan

[21] Appl. No.: 864,488

[22] Filed: Apr. 7, 1992

Related U.S. Application Data

[63] Continuation-in-part of Ser. No. 476,575, Oct. 20, 1989, abandoned, which is a continuation-in-part of Ser. No. 139,298, Dec. 28, 1987, abandoned, which is a continuation-in-part of Ser. No. 814,667, Dec. 30, 1985, abandoned.

[30] Foreign Application Priority Data

Jul. 9, 1984 [JP] Japan ................................. 59-187595
Jul. 9, 1984 [JP] Japan ................................. 59-187596

[51] Int. Cl.$^5$ ............................................. C07C 51/12
[52] U.S. Cl. ..................................................... 562/419
[58] Field of Search ......................................... 562/419

[56] References Cited

FOREIGN PATENT DOCUMENTS 53-018534  2/1978  Japan .

OTHER PUBLICATIONS

Abstract of Japanese Patent 53 018-534 dated Feb. 20, 1978.

Primary Examiner—Michael L. Shippen
Attorney, Agent, or Firm—Scully, Scott, Murphy & Presser

[57] ABSTRACT

A method for producing α-(p-isobutylphenyl)-propionic acid with a high selectivity and high purity. The method is characterized in that α-(p-isobutylphenyl)-propionaldehyde is oxidized at temperatures not higher than −12° C. in the presence of an acid using a hypohalogenite. The acid is an inorganic acid such as sulfuric acid, phosphoric acid and hydrochloric acid and the hypohalogenite may be sodium salts, potassium salts or calcium salts of hypochlorous acid or hypobromous acid.

9 Claims, 1 Drawing Sheet

METHOD FOR PRODUCING
α-(P-ISOBUTYLPHENYL) PROPIONIC ACID

CROSS REFERENCE TO RELATED APPLICATION

This application is a continuation-in-part of U.S. patent application Ser. No 476 575 filed Oct. 20, 1989, now abandoned, which is a continuation-in-part of U.S. patent application having Ser. No. 139,298 filed Dec. 28, 1987 now abandoned which is a continuation-in-part of U.S. patent application having Ser. No. 814,667 filed Dec. 30, 1985, now abandoned.

BACKGROUND OF THE INVENTION (1) Field of the Invention

This invention relates to a method for producing α-(p-isobutylphenyl)propionic acid. More particularly, the invention relates to a method for producing α-(p-isobutylphenyl)propionic acid by oxidizing α-(p-isobutylphenyl)propionaldehyde with a hypohalogenite at temperatures not higher than $-12°$ C. in the presence of an inorganic acid.

(2) Description of the Prior Art

The α-(p-isobutylphenyl)propionic acid (IPA) prepared according to the method of the present invention is known as a useful medicine for the relief of pain, fever and inflammation with little adverse reaction.

There are proposed many kinds of methods for producing IPA by oxidizing α-(p-isobutylphenyl)-propionaldehyde (IPN) with various oxidizing agents. For example, silver compounds are used as oxidizing agents in the methods disclosed in U.S. Pat. No. 3,965,161, French Patent No. 1,545,270, and Japanese Laid-Open Patent Publication No. 58-35140; permanganates are used in the methods disclosed in Japanese Laid-Open Patent Publication Nos. 51-100042, 51-101949 and 52-97930; and oxidizing agents such as chromic acid, peracids, hydrogen peroxide and chlorites are used in the method disclosed in British Patent Nos. 1,549,140 and 2,004,543 and Japanese Laid-Open Patent Publication No. 51-10042. These methods are, however, not satisfactory in view of industrial working, because the selectivity relative to the intended IPA is low or expensive substances must be used as oxidizing agents.

Japanese Laid-Open Patent Publication No. 53-18534 also discloses an oxidizing method, in which the hypohalogenite is used as the oxidizing agent in the presence of acetic acid. This method has, however, critical drawbacks owing to the acetic acid, details of which are mentioned later on.

The inventors of this application have carried out extensive studies on the oxidation using the salts of hypohalogenous acids.

As a result, the following facts were found out when only hypohalogenite as an oxidizing agent for IPN is employed. That is, (1) The by-production of halides of IPA (IPA halides) as trace impurities cannot be avoided.

(2) As the main by-product is p-isobutyl acetophenone (BAP), the ratio of IPA/BAP must be improved.

(3) It is necessary to select co-existing acids with which the aimed product of IPA can be recovered efficiently.

Therefore, the selection of a more efficient method is an important factor.

Incidentally, the substance prepared by the method of the present invention is a medicine used for the relief of fever and pain. Accordingly, it is an important matter to avoid by-production of halogenated impurities, even when the quantities of them are very small. What is worse, the chemical structure of this IPA halide is close to that of IPA.

With the above consideration, the inventors of the present application found out the following important facts and accomplished the method for efficiently producing highly pure IPA.

(1) To improve the ratio of IPA/BAP.

(2) To decrease the quantity of by-produced IPA halide.

(3) To use an inorganic acid as a co-existing acid in order to recover efficiently the aimed product.

BRIEF SUMMARY OF THE INVENTION

It is, therefore, the primary object of the present invention to provide an improved method for producing α-(p-isobutylphenyl)propionic acid.

Another object of the present invention is to provide a method for producing α-(p-isobutylphenyl)-propionic acid in which IPA containing lesser quantity of halogenated impurity can be produced in a high selectivity and the isolation of the product is quite easy.

In accordance with the method of the present invention, α-(p-isobutylphenyl)propionic acid is prepared by oxidizing α-(p-isobutylphenyl)-propionaldehyde using a hypohalogenous acid salt (hypohalogenite) in the presence of an inorganic acid at reaction temperatures of $-12°$ C. or below.

BRIEF DESCRIPTION OF THE DRAWING

These and other objects, features and advantages of the present invention will become more apparent from the following description taken in connection with the accompanying drawing in which.

DETAILED DESCRIPTION OF THE INVENTION

Figure 1:
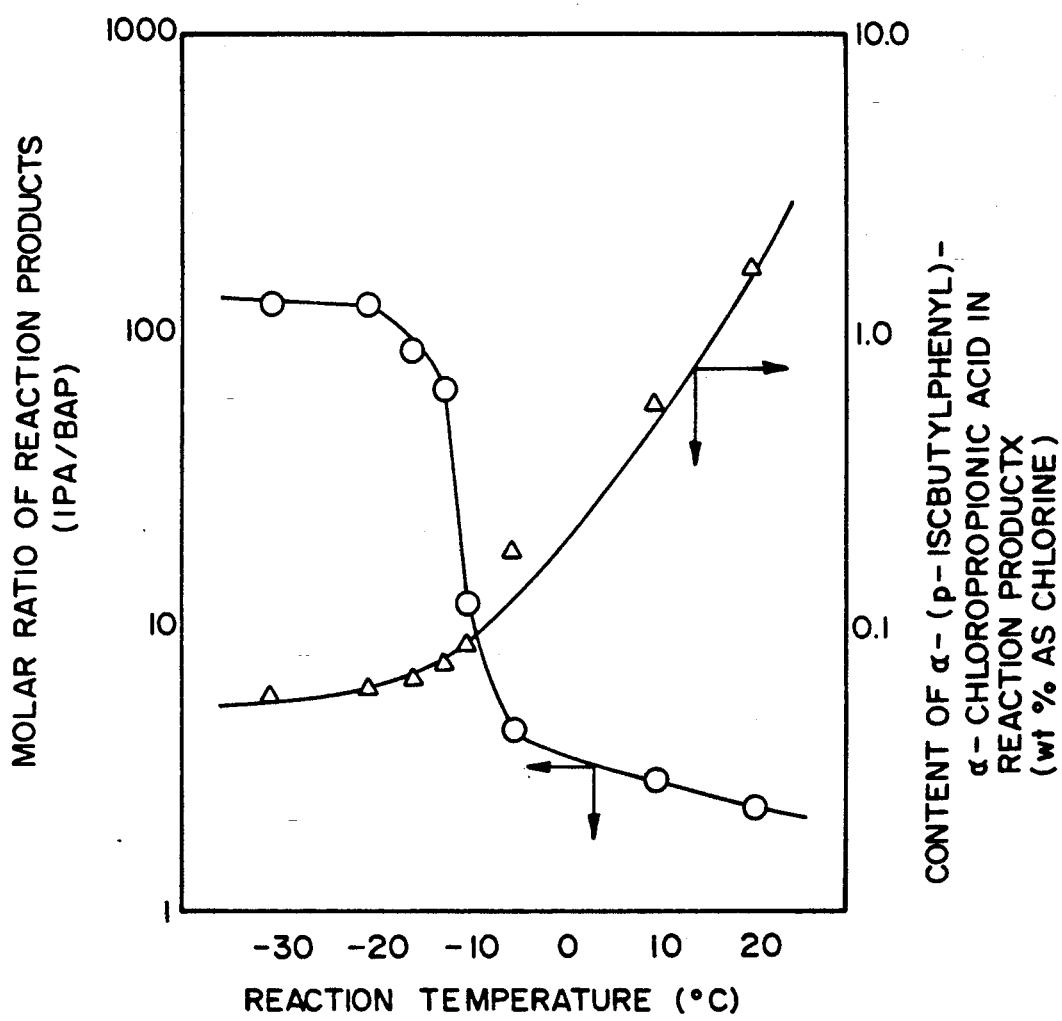
FIG. 1 is a graphic chart showing the relationship between reaction temperatures and molar ratios of reaction products (aimed product/by-product).

In the method of the present invention, hypohalogenites are used, which are exemplified by sodium hypochlorite, potassium hypochlorite, calcium hypochlorite, sodium hypobromite, and potassium hypobromite. These hypohalogenites can be used in the form of either solid salts themselves or aqueous solutions of them.

In the oxidation reaction according to the present invention, the hypohalogenite serves as an oxidizing agent almost quantitatively to give an intended product with a high selectivity. Accordingly, it is sufficient that the use quantity of hypohalogenite is almost the same moles as the moles of IPN. Even when a quantity less than equimolar amount of hypohalogenite is used, there is no problem because an aimed product and unreacted IPN can be recovered without difficulty. In view of process efficiency, however, it is desirable that more than 0.9 molar equivalent is used. When hypohalogenite is used in large excess, the remaining hypohalogenite that was not consumed for oxidation causes halogenation of the final product to reduce sometimes its purity. Therefore, it is preferable that the quantity of hypohalogenite is less than 2 moles, more preferably less than 1.5 moles, to one mole of IPN.

In the present invention, the reaction temperature is an important factor which has influences on the by-pro duction of IPA halide, the selectivity and the yield of the reaction.

The oxidation with hypohalogenite can proceed smoothly irrespective of reaction temperatures giving a high reaction rate of 99 to 100%. At higher reaction temperatures, much p-isobutylacetophenone (BAP) is by-produced. Meanwhile, the molar ratio IPA/BAP, which shows the selectivity between the intended IPA and by-product BAP, changes critically near the reaction temperature of $-12°$ C. That is, if a reaction temperature is lowered below $-12°$ C., the selectivity to IPA rises abruptly. Accordingly, desirable reaction temperatures are not higher than $-12°$ C., and preferably lower than $-15°$ C. In spite of the high value in the reaction rate irrespective of temperatures, the fact that the molar ratio of IPA/BAP changes critically is considered to be related to oxidation reaction mechanism itself, however, the detailed reason for this reaction is not understood. Such the critical change in the molar ratio is a novel concept that has been found out for the first time in the present invention. There is observed no lower limit of the reaction temperature, however, it may be $-50°$ C. in practice, because, when an aqueous solution of hypohalogenite is used, the reaction will take longer time due to the coagulation of the aqueous solution.

In the oxidation with hypohalogenite in the method of the present invention, it was understood that the chlorine liberated from the oxidizing agent itself acts on IPA and the by-production of IPA halide cannot be avoided, even though the amount thereof is trace. In the mechanism of the formation of by-product IPA halide, when the free chlorine acts on IPA, the chlorine acts on all of 7 kinds of chemically different hydrogen atoms in IPA molecule. However, it was found out that chlorine mostly acts on the hydrogen atoms bonded to the tertiary carbon atoms adjacent to the carbonyl of propionic acid group. In other words, the most part of halogenated IPA is $\alpha$-(p-isobutylphenyl)-$\alpha$-chloropropionic acid. The below-mentioned oxidation temperature has a critical influence on this act of chlorine to form the IPA impurity, that is, the formation of the impurity of IPA halide increases markedly at temperatures above $-12°$ C. Accordingly, from this viewpoint, it is necessary that the reaction of the present invention must be carried out at lower temperatures.

The reaction is carried out in the presence of an inorganic acid. Preferable inorganic acids are protonic acids such as sulfuric acid, phosphoric acid and hydrochloric acid. These acids can be employed either singly or in combination of two or more kinds. The quantity of the inorganic acid to be used is not especially limited, that is, the amount to make the reaction system neutral to acidic is sufficient. In general cases, 0.1 equivalent or more, preferably more than 0.2 equivalent of inorganic acid is used to 1 mole of hypohalogenite. However, it is not necessary to use excess amount of the acid and, in practice, the upper limit of the inorganic acid is 50 times or less equivalents relative to the moles of hypohalogenite.

As for the reaction mixture after oxidation, it comprises the main components of IPA as the aimed product, BAP as a by-product and an acid as a catalyst, and the residue of the oxidizing agent. Incidentally, because the aimed product IPA is one of organic acids, in the case that the used acid catalyst is an organic acid such as acetic acid, at least a part of the acetic acid is dissolved in the IPA. Though the by-product BAP is also dissolved in IPA, the quantity of BAP is quite small in the present invention as described above, and the separation of BAP is easy which is facilitated by the fact that BAP is not an acid. Accordingly, in order to obtain highly pure IPA at a high yield without loss, the separation of the acid as a catalyst from the IPA is important.

When an inorganic acid is used as the coexisting acid, the separation of the acid from IPA can be made easy because it is possible to take the advantage of the differences in properties between organic acids and inorganic acids.

More particularly, when an inorganic acid is used, the separation of the acid from the product IPA is quite easy, which fact much improves the efficiency in industrial practice. That is, the inorganic acids used in the method of the invention are water-soluble but they are insoluble to ordinary organic solvents. Accordingly, IPA can be easily separated from the acids by extraction with organic solvents or by washing with water. Even when the acid remains in the finally obtained IPA crystals, the acid can be easily removed by washing the product with water.

Meanwhile, organic acids such as acetic acid are water-soluble and also soluble to most of organic solvents. Therefore, acetic acid cannot be removed from IPA by simple extraction or water-washing. When IPA is rinsed with water, in order to remove the acetic acid remaining in the finally obtained IPA crystals, the IPA dissolves into the acetic acid-water solution system, which fact causes the difficulty and the loss in the recovering of IPA.

Therefore, in industrial practice, the acids used in the method of the invention are inorganic acids that are soluble in water and insoluble in organic solvents used for the extraction with the solvents.

In the oxidation, a solvent which is inert to the reaction, which neither coagulates nor freezes at lower temperatures and which has sufficient solubility to IPA, can be used. Such solvents are exemplified by water miscible solvents of ketones such as acetone and methyl ethyl ketone, ethers such as tetrahydrofuran, dioxane and diglyme, and alcohols such as methanol, ethanol and ethylene glycol; and water immiscible solvents of paraffins such as hexane, naphthenes such as cyclohexane, and aromatic hydrocarbons such as benzene and toluene. Among them, water miscible solvents produce more desirable results.

After the reaction, the reaction medium is removed under reduced pressure if necessary, and extraction of reaction mixture is done using aqueous alkali or an organic solvent to obtain IPA. As the solvents for extraction, ordinary organic solvents such as chloroform and ether can be employed. These organic solvents generally dissolve organic acids but they hardly dissolve inorganic acids.

After the extraction, the extraction solvent is removed by distillation or evaporation of the conventional method and re-crystallization is then carried out using an adequate solvent such as n-heptane to obtain a highly pure IPA at a high yield.

As described above, in the method of the present invention, $\alpha$-(p-isobutylphenyl)propionic acid (IPA) can be prepared by oxidizing $\alpha$-(p-isobutylphenyl)-propionaldehyde (IPN) in the presence of a specific acid and under a specific condition, in which the treatment of the product after reaction is easy and the rate of reaction is not lower than 99% with a high selectivity.

The present invention will be described in more detail with reference to several experiments.

EXPERIMENT 1

Several sets of 200 ml flasks with a stirrer were provided. To each flask was added 10 g (53 mmol) of IPN, 17 g of phosphoric acid (0.52 equivalent, this corresponds to 8.9 equivalents to 1 mole of hypohalogenite used), and 30 ml of a solvent, acetone. They were cooled to the respective temperatures that are shown in FIG. 1. At each temperature, 42.8 g of 10% aqueous solution of sodium hypochlorite (58 mmol as sodium hypochlorite) was added dropwise slowly. After the dropwise addition, the reaction was continued for further 1 hour. After the reaction, the oily layer was analyzed by liquid chromatography to determine the reaction rate and the molar ratio of IPA/BAP.

The reaction rates were as high as 98 to 100% at the respective reaction temperatures. As the indication of selectivities to the reaction product, the molar ratios of IPA/BAP were plotted on FIG. 1. As will be understood from the chart, the molar ratio of IPA/BAP changes critically in the reaction temperature range of $-10°$ to $-12°$ C. This shows that the selectivity to the product IPA is markedly improved in the reaction temperature range of $-12°$ C. and below.

ISOLATION OF IPA

In the above reaction procedure, the reaction product obtained at the reaction temperature of $-15°$ C. was taken. The solvent, acetone, was removed under a reduced pressure of 20 mmHg at 50° C. Extraction was done three times using each 50 ml of chloroform. The chloroform was removed by reduced pressure evaporation to obtain 10.3 g of pale yellow crude crystal of which the melting point was 70°–74° C.

The obtained crude crystal was analyzed by liquid chromatography to determine the content of α-(p-isobutylphenyl)-α-chloropropionic acid as chlorinated IPA. As the chlorinated impurities, contents of α-(p-isobutylphenyl)-α-chloropropionic acid as chlorine were plotted on FIG. 1 together with the molar ratio of IPA/BAP. This FIGURE shows that the purity of the crude IPA are markedly improved in the reaction temperature range of $-12°$ C. and below.

The above obtained crude crystal was recrystallized from n-heptane to obtain white crystal. This had a melting point of 76°–77° C. which value was the same as that of an authentic sample.

Furthermore, the obtained crystal was analyzed by Wickbold Test Method (oxyhydrogen flame combustion method), however, no $PO_4$ radical was detected.

COMPARATIVE EXAMPLE 1

Reaction was carried out at $-15°$ C. in the like manner as Experiment 1 except that 31.2 g of acetic acid was used in place of the phosphoric acid. The amount of acetic acid was 0.52 equivalent which was the same equivalency as the phosphoric acid used in Experiment 1.

It was understood by liquid chromatographic analysis of the product that the rate of reaction was 98% and the selectivity on the molar ratio of IPA/BAP was 70.

ISOLATION OF IPA

Then, in the like manner as Experiment 1, crude crystal was isolated, which had a melting point of 68°–73° C. and contained 0.9 wt % (as chlorine) of chlorinated IPA.

The re-crystallization from n-heptane was conducted to obtain white crystal in the like manner as Experiment 1. This white crystal had clearly the odor of acetic acid and the melting point thereof was 69°–74° C. It was thus understood that the product in this Experiment requires additional refining step or steps to remove acetic acid.

EXPERIMENT 2

The reaction was carried out at $-15°$ C. in a 500 ml flask with a stirrer and a dropping funnel. 19 g (0.1 mol) of IPN, 9 g (0.092 mol, 0.27 eq.) of phosphoric acid and 80 ml of acetone were put into the flask. After cooling to $-15°$ C., 82.6 g (0.11 mol as sodium hypochlorite) of 10% aqueous solution of sodium hypochlorite was slowly added dropwise from the dropping funnel. After the addition, the reaction was continued for further one hour.

The solvent, acetone, was removed under reduced pressure of 20 mmHg at 50° C.

The mixture of reaction products was extracted three times using each 50 ml of chloroform. The chloroform layer was washed with 50 ml of water. The chloroform was then removed by reduced pressure evaporation to obtain 19.2 g pale yellow crude crystal. This crude crystal had a melting point of 70°–74° C. and contained 0.09 wt % (as chlorine) of chlorinated IPA. Further, the analysis for $PO_4$ radical showed that the crystal did not contain $PO_4$ radical.

EXPERIMENT 3

The reaction was carried out in the like manner as Experiment 2 except that 4.9 g (0.05 mol, 0.15 eq.) of phosphoric acid was used.

After extraction and evaporation of chloroform in like manner as Experiment 2, 18.9 g of pale yellow crude crystal was obtained. This crude crystal had a melting point of 70°–74° C. and contained 0.09 wt % (as chlorine) of chlorinated IPA. Further, the analysis for $PO_4$ radical showed that the crystal did not contain $PO_4$ radical.

COMPARATIVE EXPERIMENT 2

The reaction was carried out in the like manner as Experiment 2 except that 9 g (0.15 mol, 0.15 eq.) of acetic acid was used in place of the phosphoric acid.

After extraction and evaporation of chloroform in like manner as Experiment 2, 17.3 g of pale yellow crude crystal was obtained. This crude crystal had a melting point of 68°–73° C. and contained 0.9 wt % (as chlorine) of chlorinated IPA. Further this crude crystal obviously showed odor of acetic acid. It was thus understood that the product in this experiment (using acetic acid as co-existing acid) requires additional refining step or steps to remove co-existing acid.

This Comparative Experiment was done in accordance with the description in Japanese Laid-Open Patent Publication No. 53-18534, except that the reaction temperature and method to obtain the crude crystal (before re-crystallization).

EXPERIMENTS 4 AND 5

Reactions were carried out at $-15°$ C. in the like manner as Experiment 1 except that 35% hydrochloric acid and sulfuric acid as indicated in the following Table 1 were used in place of the phosphoric acid. The results are also shown in Table 1.

After the reaction, crystalline products were isolated from reaction mixtures in the like manner as Experiment 1, where pure crystals were obtained by simple processing.

TABLE 1

| Experiment | 4 | 5 |
|---|---|---|
| Acid Used | | |
| Name | Hydrochloric acid (35%) | Sulfuric acid |
| Quantity (g) | 12.6 | 11.8 |
| Results: | | |
| Rate of Reaction (%) | 99 | 99 |
| Yield (%) | 97.8 | 97.7 |
| Molar Ratio (IPA/BAP) | 80.4 | 74.9 |
| Melting Point (°C.) | 76-77 | 76-77 |
| Chlorine or Sulfur | None (*1) | None (*2) |

(*1): Tested by silver nitrate method. No Cl⁻ ion was detected in crystals.
(*2): Tested by Wickbold method (oxyhydrogen flame combustion method). No SO₄ radical was detected in crystals.

EXPERIMENT 6

IPN was oxidized at −15° C. in the like manner as Experiment 1 except that 133 g of 5% aqueous solution of sodium hypobromite (56 mmol as sodium hypobromite) was used. The rate of reaction was 98%.

IPA was isolated form the obtained reaction product in the like manner as Experiment 1 to obtain white crystal having a melting point of 76°-77° C.

EXPERIMENT 7

The reaction was carried out in a similar manner as Example 3 except that 68.8 g of sodium hypochlorite, 19.03 g of IPA, 4.9 g (0.15 eq.) of phosphoric acid and 80 ml of acetone were used.

The reaction product was extracted three times, each time with 50 ml chloroform. The chloroform was then removed by reduced pressure evaporation to obtain 18.9 g (91.7% yield) of crude crystal. This crude crystal had a melting point of 70°-74° C. and contained 0.08 wt % (as chlorine) by chlorinated IPA. Further no phosphate radical was detected in the crystal.

The crude crystal was re-crystallized from n-heptane to obtain white crystal of IPA 17.5 g (85.0% yield) The recrystallized product had a melting point of 76°-77° C. which is the same as that of an authentic sample. The recrystallized product contained 0.06 wt % (as chlorine) of chlorinated IPA. Furthermore, no phosphate radical was detected in the crystal.

COMPARATIVE EXAMPLE 3

The reaction was carried out in an similar manner as described in the Example in Japanese Laid Open Patent Publication No. 53-18534. More specifically, 19.03 g of IPA, 80 mL of acetone and 9.0 g (0.15 eq.) of acetic acid are mixed and 68.8 g of sodium hypochlorite is dropwise added thereto with stirring under ice cooling for over two hours, during which time the reaction medium is kept at 5°-15° C. After the dropwise addition, the reaction was stirred for an additional one hour.

The solvent, acetone, was removed under a reduced pressure of 20 mmHg at 50° C. The reaction product was extracted three times, each time with 50 ml of chloroform. The three extracts were combined and crude crystals were obtained by evaporating the chloroform under reduced pressure, to obtain 17.8 (86.4% yield). The crude material had a melting point of 68°-73° C. and contained 0.74 wt % (as chlorine) of chlorinated IPA. The crude product had prevalent odor of acetic acid.

The crude product was recrystallized as described in Example 7 by recrystallizing with n-heptane to obtain white crystals (15.4 g, 75.0% yield.) The white crystal contained 0.67 wt % (as chlorine) of chlorinated IPA. The recrystallized white crystal had a melting point of 73°-75° C. and clearly had a strong odor of acetic acid.

Thus, both the crude and recrystallized product contained acetic acid impurities.

As clearly shown by the data in Example 7 and Comparative Example 3, the IPA prepared in accordance with the present invention was formed in greater yields and in greater purity.

The above embodiments and examples are given to illustrate the scope and spirit of the instant invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A method for producing α-(p-isobutyl-phenyl)propionic acid which is characterized in that α-(p-isobutyl-phenyl)propionaldehyde is oxidized at temperatures not higher than −12° C. in the presence of an inorganic acid using a hypohalogenite.

2. The method for producing α-(p-isobutylphenyl)-propionic acid in claim 1, wherein said inorganic acid is at least one member selected from the group consisting of sulfuric acid, phosphoric acid and hydrochloric acid.

3. The method for producing α-(p-isobutylphenyl)-propionic acid in claim 1, wherein said temperatures are in the range of −15° C. to −50° C.

4. The method for producing α-(p-isobutylphenyl)-propionic acid in claim 1, wherein said hypohalogenite is at least one member selected from the group consisting of sodium salts, potassium salts and calcium salts of hypochlorous acid and hypobromous acid.

5. The method for producing α-(p-isobutylphenyl)-propionic acid in claim 1, wherein the quantity of said inorganic acid is a sufficient amount to make the reaction system neutral to acidic.

6. The method for producing α-(p-isobutylphenyl)-propionic acid according to claim 1 wherein the molar ratio of hypohalogenite to α-(p-isobutylphenyl)propionic aldehyde ranges from 0.9 to 2.0.

7. The method according to claim 6 in which the molar ratio ranges from 0.9 to 1.5.

8. The method for producing α-(p-isobutylphenyl)-propionic acid according claim 1 in which 0.1 to 50 mole equivalent of inorganic acid is present per mole of hypohalogenite.

9. The method according to claim 8 is which at least 0.2 mole equivalent of inorganic acid is present per mole of hypohalogenite.

* * * * *

UNITED STATES PATENT AND TRADEMARK OFFICE
CERTIFICATE OF CORRECTION

PATENT NO. : 5,221,766
DATED : June 22, 1993
INVENTOR(S) : Isoo Shimizu, et al.

It is certified that error appears in the above-indentified patent and that said Letters Patent is hereby corrected as shown below:

Column 1, line 8: "476 575" should read --476,575--

Column 7, line 26: "form" should read --from--

Column 7, line 43: after "yield)" insert --.--

Column 8, line 57, Claim 8: after "according" insert --to--

Column 8, line 60, Claim 9: "is" should read --in--

Signed and Sealed this

Third Day of May, 1994

BRUCE LEHMAN

*Attest:*

*Attesting Officer*  *Commissioner of Patents and Trademarks*